United States Patent
Bob et al.

(10) Patent No.: US 7,798,956 B2
(45) Date of Patent: Sep. 21, 2010

(54) ALTERNATING PROPULSION TYPE ENDOSCOPE AND CONTINUOUS DRIVE TYPE ENDOSCOPE

(75) Inventors: Konstantin Bob, Weinheim (DE); Fritz Pauker, Kissing (DE); Thomas Viebach, Pischertshofen (DE)

(73) Assignee: invendo medical GmbH (DE)

( * ) Notice: Subject to any disclaimer, the term of this patent is extended or adjusted under 35 U.S.C. 154(b) by 452 days.

(21) Appl. No.: 11/257,708

(22) Filed: Oct. 25, 2005

(65) Prior Publication Data

US 2006/0149130 A1 Jul. 6, 2006

(30) Foreign Application Priority Data

Oct. 26, 2004 (DE) ........................ 10 2004 052 036

(51) Int. Cl.
*A61B 1/00* (2006.01)
*A61B 1/04* (2006.01)
*A61M 29/00* (2006.01)

(52) U.S. Cl. ........................ 600/114; 600/115; 600/116; 604/101.04; 604/101.05

(58) Field of Classification Search ................. 600/104, 600/106, 114–116, 139, 141, 144, 148, 143, 600/151; 604/95.01, 95.02, 95.03, 95.04, 604/103, 103.01, 103.03, 103.05, 165.01, 604/101.01, 101.04, 101.05, 103.07, 106

See application file for complete search history.

(56) References Cited

U.S. PATENT DOCUMENTS

| | | | | |
|---|---|---|---|---|
| 4,040,413 A | * | 8/1977 | Ohshiro | 600/116 |
| 4,066,070 A | * | 1/1978 | Utsugi | 600/116 |
| 4,176,662 A | * | 12/1979 | Frazer | 600/114 |
| 4,577,621 A | | 3/1986 | Patel | |
| 4,693,243 A | * | 9/1987 | Buras | 128/207.15 |
| 4,815,450 A | * | 3/1989 | Patel | 600/115 |
| 5,112,310 A | | 5/1992 | Grobe | |
| 5,315,992 A | * | 5/1994 | Dalton | 128/207.15 |
| 5,337,733 A | * | 8/1994 | Bauerfeind et al. | 600/139 |
| 5,658,296 A | * | 8/1997 | Bates et al. | 606/127 |
| 5,842,971 A | * | 12/1998 | Yoon | 600/101 |
| 5,972,019 A | * | 10/1999 | Engelson et al. | 606/200 |
| 6,007,482 A | | 12/1999 | Madni et al. | |
| 6,077,219 A | * | 6/2000 | Viebach et al. | 600/114 |
| 6,461,294 B1 | * | 10/2002 | Oneda et al. | 600/116 |
| 6,464,665 B1 | | 10/2002 | Heuser | |
| 6,702,735 B2 | * | 3/2004 | Kelly | 600/115 |
| 2002/0143237 A1 | * | 10/2002 | Oneda et al. | 600/116 |
| 2003/0114803 A1 | | 6/2003 | Lerner | |

FOREIGN PATENT DOCUMENTS

| | | |
|---|---|---|
| DE | 3630660 | 3/1988 |
| EP | 1582139 | 10/2005 |

OTHER PUBLICATIONS

German Language European Search Report, issued by the European Patent Office in connection with application No. 05022928.5-2305 on Feb. 2, 2006, 5 pages.
German Language European Search Report, issued by the European Patent Office in connection with application No. 05022928.5-2305 on Jun. 9, 2006, 10 pages.
German Language Official Communication, issued by the European Patent Office in connection with application No. 05022928.5-2305 on Jul. 22, 2009, 2 pages.

* cited by examiner

*Primary Examiner*—Linda C Dvorak
*Assistant Examiner*—Alireza Nia
(74) *Attorney, Agent, or Firm*—Hanley, Flight & Zimmerman, LLC (57) ABSTRACT

An endoscope preferably comprising an alternating propulsion system in which an endoscope shaft is advanced by means of an auxiliary means (e.g. a hose preferably including fluid pads or a guiding wire/net) in a canal-shaped cavity by the fact that the endoscope shaft and the auxiliary means are alternately resting with respect to a cavity to be inspected and, at the same time, the element not at rest can be advanced while being guided along the resting element into the cavity, or are simultaneously moved forward, wherein in the latter case the basic stiffness of the auxiliary means is higher than that of the shaft.

25 Claims, 8 Drawing Sheets

ALTERNATING PROPULSION TYPE ENDOSCOPE AND CONTINUOUS DRIVE TYPE ENDOSCOPE

BACKGROUND OF INVENTION

The invention relates to an alternating propulsion type endoscope for moving an endoscope shaft along a canal-shaped cavity and to a continuous drive type endoscope.

Endoscopes have become an important aid in technology and above all in medicine to inspect canal-shaped cavities which otherwise are only accessible by considerable operations. Endoscopes are preferably used for examining the esophagus, the stomach, the duodenum from the stomach, the intestines from the anus, the urethra, the bladder and the ureter.

Such endoscopes are equipped at their leading end with a lighting means and with an optical system for visually detecting the area upstream of the cavity. The optical information detected at the leading end of the endoscope usually is either transmitted to the rear by means of fiber optics through the endoscope to its operating end or is detected by means of an optical sensor chip at the leading end, is guided to the rear via an electric line through the endoscope and is displayed on a screen. Moreover, also a transmission of information via radio from the leading end to the operating end is possible.

Furthermore, endoscopes usually comprise a working conduit, as it is called, through which various operating instruments can be introduced and operated. For instance, small forceps for taking tissue specimens, biopsy needles, heatable cutting wires, small scissors, coagulation electrodes or the like are introduced to carry out surgical measures on damaged tissue where necessary. Finally a fluid conduit for washing, and operating wires or fluid lines for bending the leading end of the endoscope in several directions are usually provided. These operating wires or fluid lines are in turn guided inside the endoscope shaft to the leading or distal end thereof.

For introducing and moving forward the endoscope shaft in the canal-shaped cavity to be inspected, DE 42 44 990 discloses a respective device. In this device a slip hose is moved along with the endoscope shaft during the forward movement of the endoscope shaft into a cavity and is slipped inside-out upon reaching the distal end so that the portion of the slip hose slipped inside-out is resting vis-à-vis the cavity wall. The advantage of this resting portion of the slip hose consists in the fact that damages of the cavity wall are reduced. Moreover, it has been assumed with this device that when applied in medical engineering, the pain for the patient can be significantly reduced due to the forward movement when the slip hose is resting relative to the intestinal wall.

However, recent examinations have shown that the principal reason for the pain during coloscopy is not the relative movement between the introduced endoscope shaft and the intestinal wall, but that the pain is mainly caused by pressing the distal end of the endoscope shaft against the curved outer wall of intestinal bends. (In this context, each of the terms curved outer wall and inner wall denotes the cavity wall lying further outside or inside with respect to a fictitious center of a cavity bend).

Therefore it is an object of the invention to realize an endoscope comprising a propulsion system of a simple design by which less pressure is exerted against the curved outer wall.

SUMMARY OF THE INVENTION

This object is achieved by an endoscope comprising an alternating propulsion system including the features of the first independent claim and by a continuous drive type endoscope including the features of the second independent claim. The invention is based on the following basic consideration.

Endoscope shafts basically have to meet two opposite conditions. On the one hand, they have to be pushed into a cavity to be examined, which requires a particular stiffness of the shaft so that it does not buckle. On the other hand, they have to be sufficiently flexible to be capable of following curvatures. The latter condition is important especially when examining intestinal walls, because a too low flexibility results in the fact that an endoscope shaft bulges the intestinal wall at an intestinal curvature which results in considerable pain, as described above.

According to an aspect of the invention, an endoscope shaft is advanced by an auxiliary means preferably in the form of a hose or hose means in a canal-shaped cavity which surrounds the shaft at the outer wall. What is decisive in this case is that this hose/hose means is or can be made stiffer at least temporarily than the preferably highly flexible endoscope shaft. This design prevents buckling of the endoscope shaft by the hose/hose means surrounding and supporting the same, simultaneously a still sufficiently high flexibility can be maintained.

Consequently, in order to realize the foregoing basic inventive idea the core of the invention consists in designing the outside hose/hose auxiliary means to be relatively movable with respect to the endoscope shaft located therein, wherein the endoscope shaft as the first element and the auxiliary means as the second element are alternately resting with regard to a cavity to be inspected, i.e. they do not move forward, and simultaneously the element not resting at the moment can be advanced into the cavity while being guided along the just resting element.

In this case it is advantageous if to one of the two elements, preferably the hose/hose means surrounding the endoscope shaft, only temporarily a higher stiffness is imparted than that of the endoscope shaft. To put it more concretely, the basic stiffness of the hose is lower than that of the endoscope shaft. In this situation the endoscope shaft serves as a guide element, i.e. the endoscope shaft is capable of guiding the hose moving relative to the former also through curvatures. Moreover, the hose includes a device by means of which the flexible hose can be stiffened, especially to reach such stiffness which is higher than that of the endoscope shaft.

In this situation the hose serves as a guide element, i.e. the hose is capable of guiding the shaft moving relative to the former through curvatures. Those skilled in the art have a plurality of such devices for optional (temporary) (alternating) stiffening of the hose and/or the shaft at their disposal. For instance, the endoscope shaft and/or the hose can be lined or covered with fluid pads or canal-shaped cavities extending in the longitudinal direction or spirally, the content (volume) of which can be optionally increased and released again. It is also possible, for instance, to use fluids whose physical state of solid-liquid is variable within a particular temperature range.

Finally another variant is mentioned according to which the hose means consists of a plurality of (at least two) hoses arranged inside each other which are movable, each per se, relative to each other and relative to the shaft (in a telescopic manner). The stiffness of preferably each of the plurality of hoses is lower than that of the shaft, whereas in their entirety they reach a higher stiffness than the shaft, i.e., as soon as the shaft has been advanced into the cavity to be examined by a particular distance, the plurality of hoses are tracked successively each individually, wherein the shaft can take over a guiding function for each individual hose (because of the higher stiffness). After that the hoses are individually advanced beyond the leading end of the shaft by a predetermined distance and are then held in a superimposed position. Now the plurality of hoses has a total stiffness which is higher than that of the shaft so that they are capable of jointly guiding the tracked shaft Further advantageous configurations of the invention are the subject matter of the other claims.

BRIEF DESCRIPTION OF THE DRAWINGS

Hereinafter the invention is described in detail by way of preferred embodiments with reference to the enclosed drawings, the following being schematically illustrated in the drawings.

DETAILED DESCRIPTION OF THE PREFERRED EMBODIMENTS

By way of the FIGS. 1 to 3C the endoscope with alternating propulsion is described in detail according to a first embodiment. In accordance with this embodiment, the endoscope according to the invention comprises a flexible endoscope shaft 1 to the distal end of which an endoscope head 2 is attached and to the other end (operating end) of which operating devices and, where appropriate, information evaluating devices (not shown) are connected. This endoscope head 2 may include various means 3, such as for instance an optical system, a lighting means, a working conduit for different tools, etc.

Figure 1:
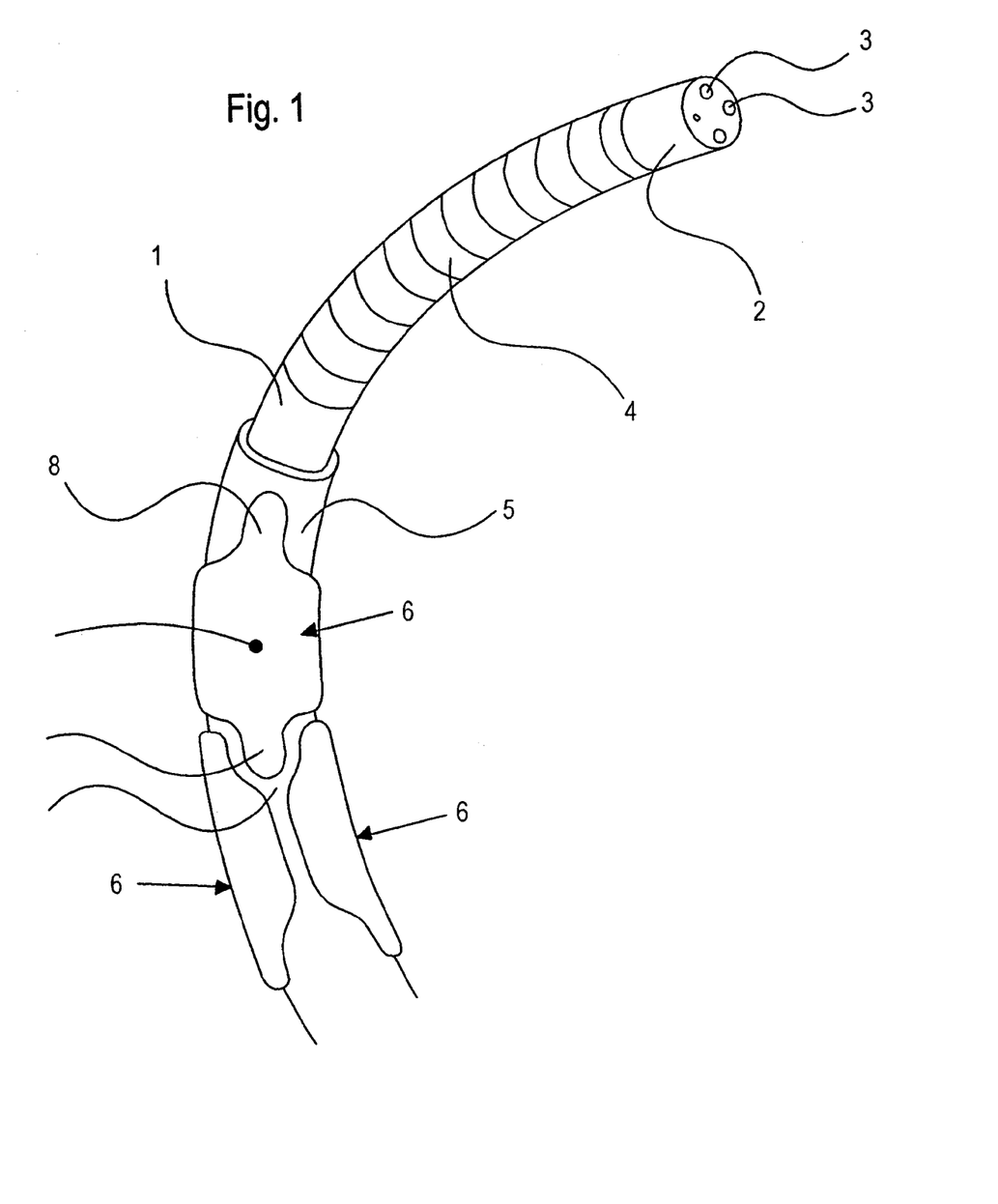
FIG. 1 is a spatial representation of a first embodiment of the endoscope of the present invention.

The endoscope head 2 is preferably connected to the flexible endoscope shaft 1 by a movable distal end portion 4 (hereinafter referred to as a "deflecting"). The deflecting 4 can be bent in several radii of curvature, preferably in several directions, in response to the instructions from the operating end (not shown) of the endoscope. Here a conventional deflecting is employed, as it is described, for instance, in the applications DE 102 09 986 A1 or DE 100 10 932 A1. Concerning the exact functioning and design of this deflecting reference is made to these applications. In this context, it is merely stated that, as already mentioned, the deflecting can be bent by control signals and/or pressures from the operating end and thus can also be optionally stiffened in this bent position or in a not bent position.

The lines (not shown) for controlling the deflecting 4 and the means 3, as well as possibly provided working conduits for operating and introducing tools used at the endoscope head 2, extend inside the deflecting 4 and the endoscope shaft 1 backwards to the operating end.

The endoscope shaft 1 is preferably surrounded by a preferably single-wall hose 5 up to the position at which the endoscope shaft 1 is connected to the deflecting 4 so that the deflecting 4 including the endoscope head 2 connected thereto projects from the leading end (distal end) of the hose 5. In this embodiment the hose consists of EPTFE material having a wall thickness of 2 to 3 mm. For reinforcement a spiral spring can be introduced in the hose-shaped EPTFE material such that the EPTFE hose material extends conically with respect to the spiral spring and the spring wire (not necessarily made of spring steel) is completely embedded in EPTFE material between the inner hose wall and the outer hose wall. Moreover, it is also possible to arrange the spiral spring conically with respect to the EPTFE material, wherein the spiral spring is enclosed with the EPTFE hose material and is connected to the same so that the spiral spring is exposed to the inside. Furthermore, the spiral spring is not absolutely necessary and a design of the hose 5 without spiral spring is imaginable, too. The hose material is not restricted to said EPTFE material, either, and may be made of other materials such as silicone, for example.

In this embodiment the hose 5 is provided with fluid pads 6 at the outer circumference. These fluid pads 6 preferably have an oblong design and are broadened at the central portions 7 thereof. Thus the fluid pads 6 have at their leading end and their trailing end a narrow tongue-shaped end portion 8.

In the present embodiment the fluid pads 6 are arranged in groups, each consisting of three fluid pads 6. The fluid pads 6 of this group of three are aligned in parallel to each other about the outer circumference of the hose 5 so that the side faces of the fluid pads 6 contact each other at their central portion 7 or form a small clearance. That is to say, this group of three fluid pads is distributed around the outer circumference of the hose such that the mean perpendiculars of the fluid pads 6 intersect the central axis of the endoscope shaft 1 and form an angle of 120° with respect to the mean perpendicular of the respective neighboring fluid pad 6. Thus, in this group the tongue-shaped end portions 8 project at a distance of 120° (in a plane normal to the central hose axis) to the front and to the rear distribute around the outer circumference of the hose 5. Since the end portions 8 are narrower than the central portions 7, an end portion is further spaced apart from the respective neighboring end portion than the respective central portions 7. In this way bulges 9 are formed between two respective neighboring end portions 8.

Adjacent to the above-mentioned group of three fluid pads 6 another group of three fluid pads 6 is arranged ahead of and behind the former in such manner that the end portions 8 of the latter group of three fluid pads 6 are inserted in the bulges of the former group of three fluid pads 6. That means that fluid pad groups adjacent in the longitudinal direction are offset by 60° in the circumferential direction in a plane normal to the central hose axis.

The fluid pads 6 are arranged in accordance with the aforedescribed way approximately along an end portion of 50 cm in length of the hose 5 starting from the leading end thereof.

Pressure has to be applied to the fluid pads 6 via feed lines (not shown) extending in the wall or at the inner or outer circumference of the hose 5 backwards to the operating end.

Depending on the pressure applied to the fluid pads 6 the flexibility of the hose 5 can be varied. Moreover, the air pads 6 get in contact with the wall of the cavity so that the hose 5 is stationary vis-à-vis the wall of the cavity. Thus, the application of pressure to the fluid pad 6 and/or a relief of incompressible fluid in the fluid pad 6 permits to optionally impart flexibility to the hose 5 which is lower or higher than the flexibility of the endoscope shaft 1 as well as to simultaneously put the hose 5 into a stationary or movable condition vis-à-vis the cavity wall.

Due to the fact that the air pads overlap at the tongue-shaped end portions 8, the hose 5 can be supported at the entire circumference of the cavity wall without loosing its flexibility.

Figure 2:
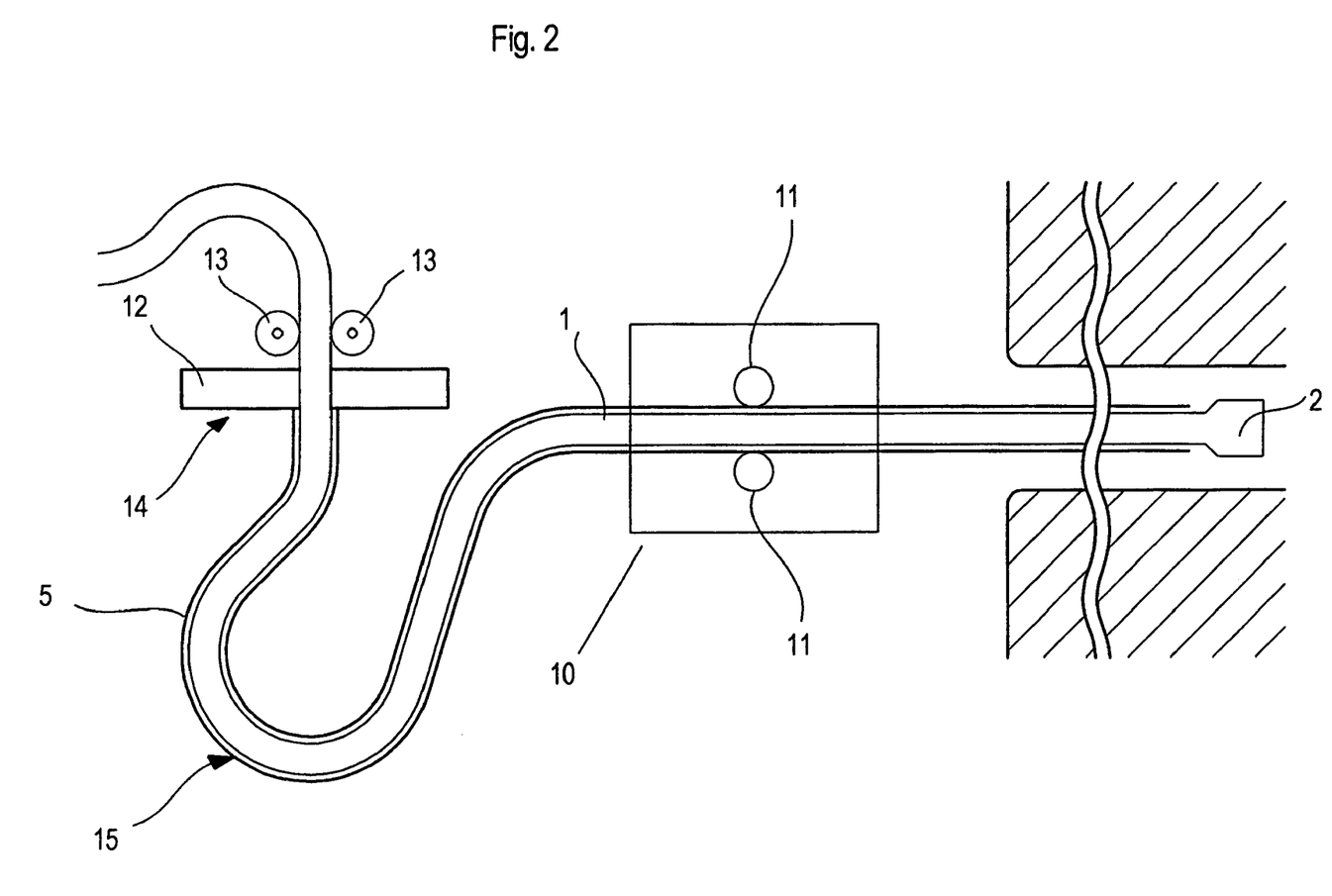
FIG. 2 shows drive means for moving the endoscope forward according to the first embodiment.
Figure 3:
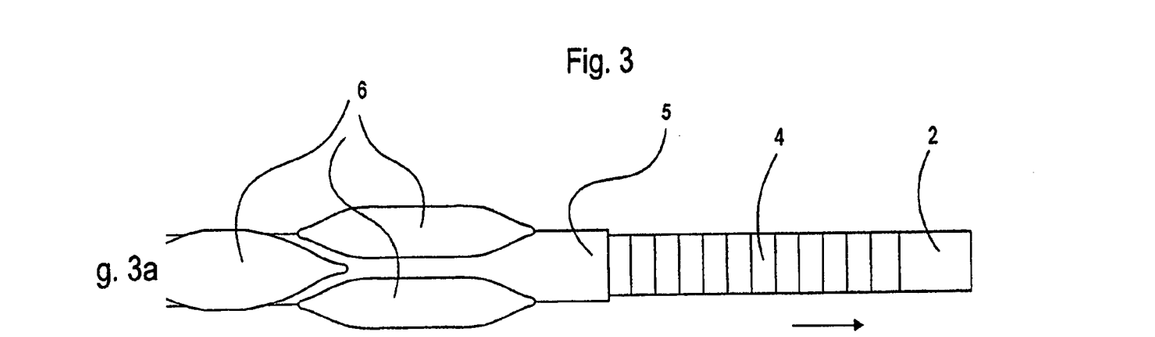
FIGS. 3a to 3c are front views of the endoscope illustrating the progressive movement of the endoscope according to the first embodiment.

FIG. 2 shows the endoscope in a state in which it has already been moved a bit into the cavity. Reference numeral 10 denotes a first drive means 10 for a progressive movement of the hose 5. The drive means 10 comprises a pair of drive wheels 11 which are frictionally engaged from two sides with the hose 5 by their groove-shaped outer circumference. These drive wheels 11 are driven by an electric motor which is not shown. The hose 5 is fastened to a plate-shaped member 12 by its trailing end. Between the first drive means 10 and the plate 12 the endoscope shaft 1 is laid with the surrounding hose 5 into a bulged shape 15. In the area of the plate 12 lubricating material might be pressed into the space between the endoscope shaft 1 and the hose 5.

At the side of the plate 12 opposed to the hose 5 preferably a pair of drive wheels 13 is provided which are frictionally engaged from two sides with the endoscope shaft 1. These drive wheels 13 form a second drive means 10 together with an electric motor, which is not shown, and the plate 12 connected to the drive wheels 13.

The first drive means 10 is fixedly connected to the second drive means 14 so that these drive means cannot move, relative to each other. Moreover, these drive means 10, 14 have to be arranged with respect to the cavity to be examined such that they do not move relative to the cavity.

The surface of the drive wheels 11 at their groove-shaped outer circumference is designed such that great friction occurs between the drive wheels 11 and the hose 5. Between the hose 5 and the endoscope shaft 1 either lubricating material is introduced and/or the endoscope shaft 1 is coated (e.g. Teflon) such that a minimal friction occurs between the hose 5 and the endoscope shaft 1. Thus it is possible that the hose 5 is frictionally driven by means of the drive wheels 11, while the endoscope shaft 1 is moved into the opposite direction by the drive wheels 13 or is at rest.

(Functioning of the First Embodiment)

The functioning of the first embodiment is described with reference to FIGS. 2 and 3a-3c.

In FIG. 3a the endoscope shaft 1 and the hose 5 are provided at a particular position of a cavity to be inspected. The fluid pads 6 are filled with fluid by the pump (not represented) and thus get into contact with the cavity wall. Due to the pressure of the fluid pads 6 against the cavity wall the hose 5 is stationary with respect to the cavity wall. In addition or alternatively, the hose 5 is held by the drive means 10. Moreover the fluid supply is controlled in such manner that the hose 5 has a lower flexibility (higher stiffness) than the endoscope shaft 1 when the filling of the fluid pads is completed.

Based on this state, the endoscope shaft 1 is moved forward by means of the second drive unit 14. The first drive unit 10 is idling. This operation is schematically represented in FIG. 3b. When the endoscope shaft 1 is moved forward, the hose 5 serves as a supporting conduit for the movement of the endoscope shaft 1. This supporting effect is assisted by the lower flexibility of the hose 5.

If it is necessary during this progressive movement of the endoscope shaft 1 to guide the front portion of the endoscope shaft 1 along a bend of the cavity, it is proceeded as follows. First of all the cavity bend can be detected at the endoscope head 2 by sensors or by the optical system installed in the endoscope head. When the endoscope head 2 is moved forward along the bend of the cavity, the curvature of the deflecting 4 can be adjusted and adapted to the radius of curvature of the cavity bend. Thus, no pressure or only low pressure is exerted on the curved outer wall of the cavity. When the endoscope head 2 has reached an end of the cavity bend, the deflecting 4 is straightened upon the further forward movement of the endoscope head 2.

When the endoscope shaft 1 has been moved out of the hose 5 (has advanced) over a particular predetermined distance by means of the second drive unit 14, the second drive unit is stopped, whereby the shaft 1 is retained.

The further progressive movement is shown in FIG. 3c. Accordingly, the fluid pads 6 are relieved so that the hose 5 is movable with respect to the cavity wall. Moreover, when the fluid pads 6 are relieved the hose 5 has a higher flexibility than the endoscope shaft 1. In this state the hose 5 is moved forward by the first drive means 10. During this progressive movement the bulged shape 15 of endoscope shaft 1 and hose 5 becomes smaller. By the fact that the drive means 14 retains the endoscope shaft 1 it is obtained that the endoscope shaft 1 is resting with respect to the cavity to be inspected, while the leading end of the hose 5 moves in the direction of the leading end of the endoscope shaft 1 (concerning the progressive movement of the hose 5 several modifications are possible which are described at the end of this description).

During this progressive movement of the hose 5 the endoscope shaft 1 resting with respect to the cavity acts with its lower flexibility (higher basic stiffness compared to that of the hose 5) as a rail for the hose 5. Since the endoscope shaft 1 is provided further inside the cavity than the hose 5, at the time when the hose 5 starts moving the endoscope shaft 1 has already adopted the shape of the cavity, through which the hose 5 passes in one cycle, with all possible bends. When, thus, the hose 5 follows the shape of the endoscope shaft 1, the force by which the hose 5 presses against the curved outer wall can be reduced. In the present invention, the force otherwise pressing against the curved outer wall is deflected by the endoscope shaft 1 which is stiffer in this state. For use in medicine this means at the same time that the pain felt by the patient does not occur or is reduced.

Preferably the hose 5 is moved forward, as represented in FIG. 3c, until the leading end of the hose 5 reaches the connecting point between the hose 5 and the deflecting 4. After completion of such a cycle of movement as described by way of the FIGS. 3a to 3c, the progressive movement of the endoscope is continued in a new cycle starting with FIG. 3a. That is to say, the fluid pads 6 are filled again so that the hose 5 is stationary relative to the cavity wall. Subsequently the endoscope shaft 1 is moved forward, etc.

This alternating propulsion of the endoscope shaft 1 and the hose 5 is repeated until the desired location to be examined in the cavity is reached.

The endoscope can be moved backward by reversing the course of the forward movement. Another possibility would be to relieve the fluid pads and to release the deflecting 4 such that it is freely movable. After that the endoscope shaft could be withdrawn from the cavity together with the hose 5.

Figure 4:
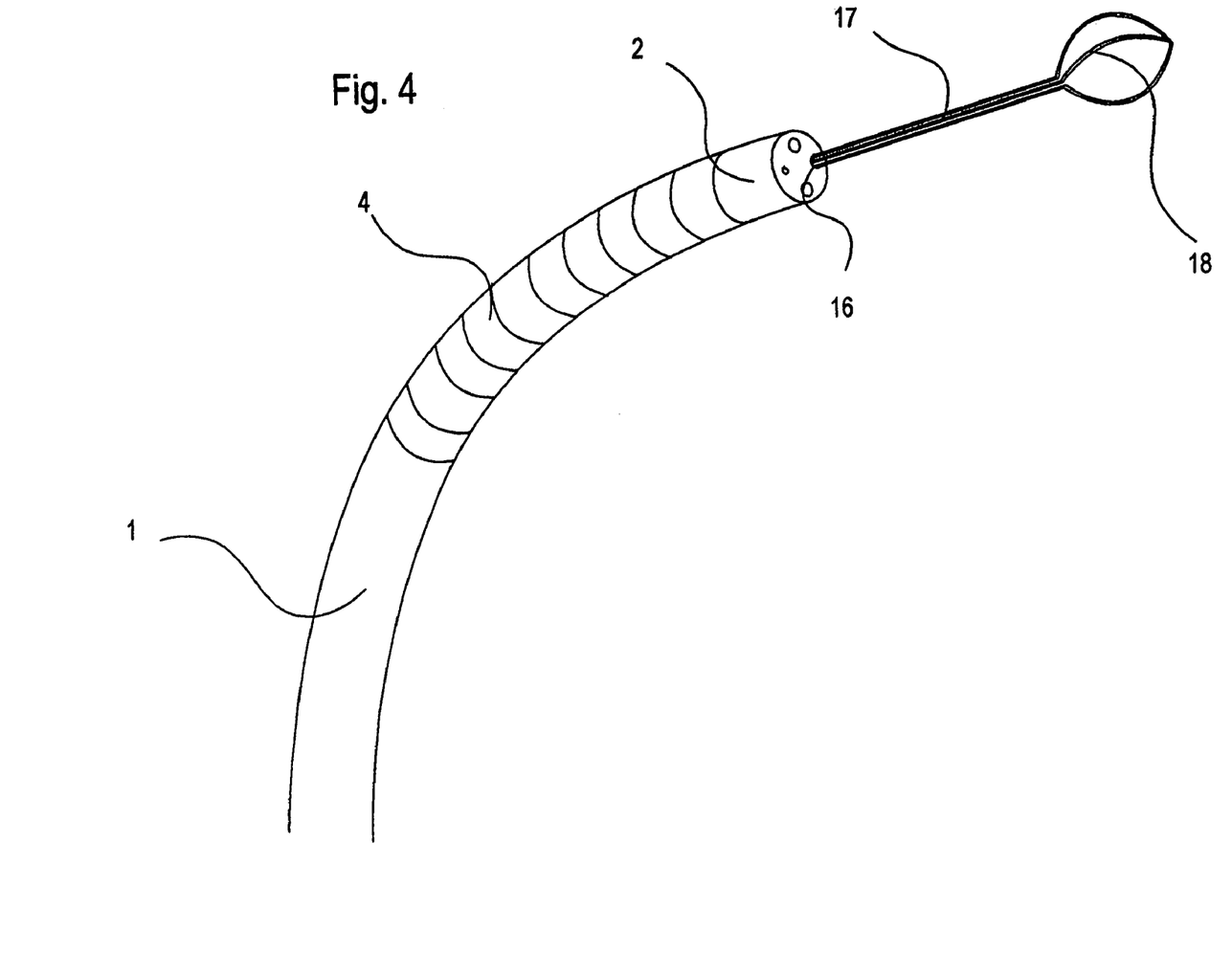
FIG. 4 is a spatial representation of an endoscope according to a second embodiment.

FIG. 4 represents a second embodiment of the present invention. In the description of this embodiment components which are equal to those of the first embodiment are denoted with the same reference numerals and the description of these components is omitted.

In this embodiment no hose including air pads is provided, instead a guiding wire 17 having a lower flexibility than the endoscope shaft 1 is guided through the working conduit 16 of the endoscope shaft 1. The guiding wire 17 is connected at its leading end to a foldable cage 18. This cage 18 can be guided through the working conduit 16 in the folded state.

When introducing the endoscope shaft 1 into a cavity to be inspected, the cage 18 and some centimeters of the guiding wire 17 project forward from the leading end of the endoscope shaft 1. Then the cage 18 is introduced visibly bit into the cavity. Subsequently the endoscope shaft 1 is advanced by a drive or manually, while the guiding wire 17 including the cage 18 is brought into a rest position vis-à-vis the cavity, for instance by holding the rear end of the guiding wire 17 in place.

During the forward movement of the endoscope shaft 1 the guiding wire 17 resting vis-à-vis the cavity serves as a rail for the endoscope shaft 1. Thus, the endoscope shaft 1 follows in its forward movement the guiding wire 17 and, in the case of a bend of the cavity, is guided along the bend without applying too high pressure to the curved outer wall. By virtue of the lower flexibility of the guiding wire 17 compared to the flexibility of the endoscope shaft 1, the forces which otherwise would be applied by the endoscope shaft 1 to the curved outer wall are deflected via the stiffer guiding wire 17.

When the endoscope shaft 1 has approached the rear end of the cage 18, the propulsion of the endoscope shaft 1 is stopped and the guiding wire 17 including the cage 18 is moved forward by means of a drive or manually, while the endoscope shaft 1 remains in a resting position vis-à-vis the cavity.

Due to the shape of the cage 18 tapered to the front, the cage can be guided along the cavity and along cavity bends without pressing too strongly against a curved outer wall and instead it follows the bend of the cavity. During its forward movement the guiding wire 17 is supported by the endoscope shaft 1. If the guiding wire 17 has been moved out of the endoscope shaft over a predetermined distance so that the cage 18 has moved forward by such predetermined distance from the leading end of the endoscope shaft 1, again the guiding wire 17 including the cage 18 is brought into a resting position vis-à-vis the cavity, while the endoscope shaft 1 is moved forward using the guiding wire 17 as a rail, etc.

This alternating propulsion of the endoscope shaft 1 and the guiding wire 17 including the cage 18 is repeated until the desired location to be examined in the cavity is reached.

Optionally the shaft or the guiding wire can be provided with temporary stiffening means as they are mentioned in the introductory part of the specification and/or as modifications.

Figure 7:
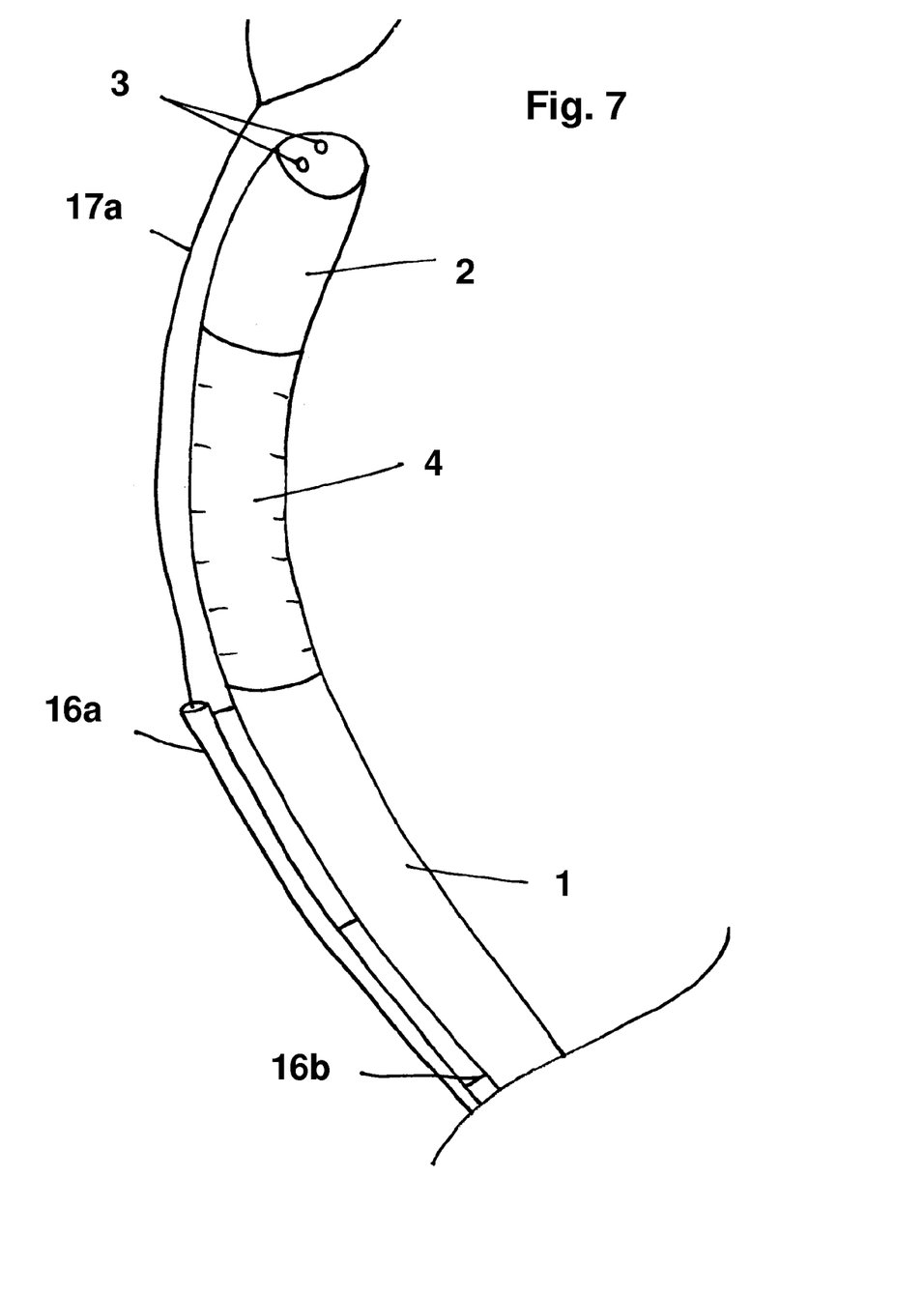
FIG. 7 shows a modification of the second embodiment of the invention.

In a modification of the aforementioned embodiment according to the invention a continuous drive type endoscope is provided which is shown schematically in FIG. 7.

It is noted that the description of parts which have been described in detail above will be omitted. These parts are designated with the same reference numerals as above.

In this modification the endoscope comprises at least an endoscope shaft 1 (which might comprise the same means as in the aforementioned embodiments) at the outer circumference of which a catheter hose 16a acting as stiffness adjusting means and as guiding means is disposed in the longitudinal direction and/or in the axial direction of the endoscope shaft 1. Preferably plural catheter hoses 16a are disposed evenly, i.e. in equal and/or regular angular distances with respect of the circumferential direction of the endoscope shaft 1 along the circumference to the endoscope shaft 1. In a preferred formation of the endoscope shaft 1, exactly three catheter hoses 16a are disposed in the above manner at the outer circumference of the endoscope shaft 1 at angles of 120°.

However, the catheter hoses 16a do not necessarily have to be disposed at the outer circumference of the endoscope shaft 1. As it can be gathered from the FIGS. 8a and 8b, the endoscope shaft 1 is shown in cross section, i.e. a sectional view in a plane perpendicular to the longitudinal direction or axial direction of the endoscope shaft 1 is given.

Figure 8A:
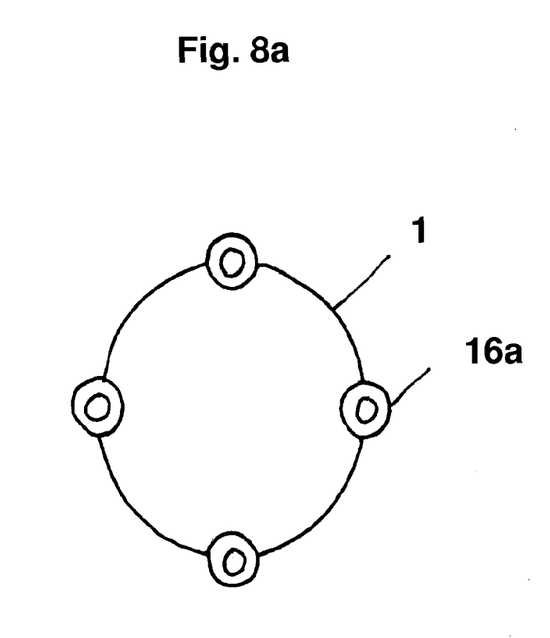
FIGS. 8a and 8b show cross-sectional views of the endoscope shaft of FIG. 7.

In FIG. 8a, the catheter hoses 16a are disposed in grooves which are formed on the outer circumference of the endoscope shaft 1 in the longitudinal direction thereof so that only a part of the catheter hoses 16a protrudes over the outer circumference of the endoscope shaft 1 in the radial direction thereof.

Figure 8B:
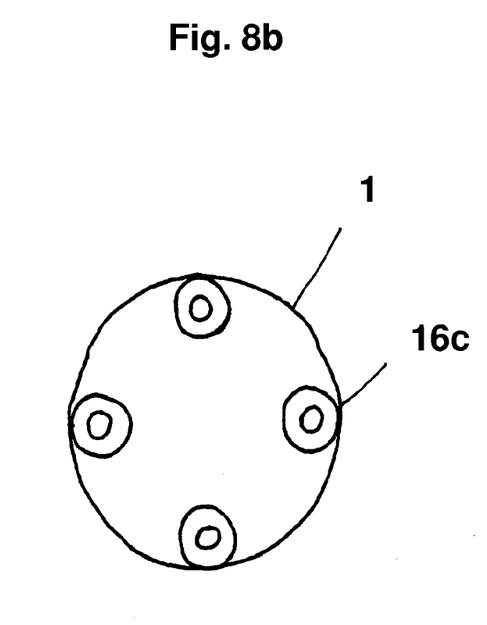

FIG. 8b shows another cross section of the endoscope shaft 1. Instead of disposing the catheter hoses 16a at the outer circumference or grooves of the endoscope shaft 1, canals 16c are formed in the interior of the endoscope shaft 1, which might be formed by catheter hoses 16a but do not have to, and extend in the longitudinal direction thereof and are preferably disposed close to the outer circumference of the endoscope shaft 1.

The endoscope shaft 1 is extremely flexible, as mentioned in the foregoing. However, it is necessary in this embodiment that it takes up mainly forces acting in a radial direction of the endoscope shaft 1. Such forces are due to the arrangement of the catheter hose 16a. Therefore preferably a wire spiral (not shown in FIG. 7) which only insignificantly impairs the bending capability of the endoscope shaft 1 but which permits taking up forces in the radial direction of the endoscope shaft 1 is incorporated in the endoscope shaft 1 in the longitudinal direction of the latter. It is noted that other devices known in prior art which permit said take-up of forces in the radial direction of the endoscope shaft 1 may equally be used.

The catheter hose 16a acting as stiffness adjusting means and as guiding means is capable of varying the stiffness of the same. Accordingly, the endoscope shaft 1 can be prevented from being bended excessively by varying the stiffness, as it will be explained in detail below. This may be effected by methods already known in prior art, as they have been mentioned, inter alia, in the foregoing.

The catheter hose 16a shown in FIG. 7 is mounted on the endoscope shaft 1 by means of supports 16b which may be known from prior art. Preferably the supports 16b hold the catheter hose 16a such that a distance and/or clearance is formed in the radial direction of the endoscope shaft 1 between the catheter hose 16a and the endoscope shaft 1, which distance or clearance is preferably within a range of from 0.5 cm to 1 cm. Thus, no relative movement of the catheter hose 16a with respect to the endoscope shaft 1 is possible (which is also the case in formations shown in FIGS. 8a and 8b). Preferably, the supports 16b are elastically deformable in the radial direction of the endoscope shaft 1, wherein the degree of deformation is adjustable by the choice of the respective supports 16b.

However, these supports 16b do not necessarily have to be arranged between the endoscope shaft 1 and the catheter hose 16a. As mentioned above, it is also possible that grooves (not shown in FIG. 7 but in FIG. 8(a)) are formed in the longitudinal direction of the endoscope shaft 1 in which the catheter hose 16a is embedded and fixedly arranged. Accordingly, the supports 16b can be omitted.

Also other attachments of the catheter hose 16b on the endoscope shaft 1 are possible as long as the catheter host 16 is able to act as stiffness adjusting means and guiding means.

Preferably, an elastic guiding wire 17a acting as guiding element is glidingly supported in the catheter hose 16a, thereby the guiding wire 17a being movable in the catheter hose 16a. At the end of the guiding wire 17a a loop 18a projecting from a distal end of the endoscope shaft 1, i.e. from a leading end of the endoscope shaft 1 with respect to the moving direction of the endoscope shaft 1 is formed. Thus, the loop 18a of the guiding wire 17a protrudes in the axial direction of the endoscope shaft beyond the distal end portion of the endoscope shaft 1 (also beyond the deflecting 4 and the endoscope head 2 of the endoscope shaft) by a predetermined distance which is variable by the frictional/sliding support. It is noted that the catheter hose 16a is only attached to the endoscope shaft 1 via the supports 16b. The deflecting 4 and the endoscope head 2 correspond to a movable distal end portion of the endoscope shaft 1 which are not in contact with the catheter hose 16a or the supports 16b. The other end of the guiding wire 17a protrudes beyond the proximal end portion of the endoscope shaft 1 (which corresponds to the operating end of the endoscope shaft 1) by a predetermined length. As described hereinafter in the detailed functional description of the endoscope, the guiding wire 17a is operated by the end of the guiding wire 17a protruding from the proximal end portion of the endoscope shaft 1 for shifting the guiding wire 17a and thus for shifting the loop 18a provided at the distal end portion of the endoscope shaft 1. In an alternative embodiment of the loop 18a the dimension thereof, i.e. the size of the loop 18a is variable as in the aforementioned second embodiment (cf. the foldable cage 18 of the second embodiment).

The end of the guiding wire 17a projecting from the distal end portion of the endoscope shaft 1 may equally consist of plural loops 18a which are arranged with respect to each other such that a spherical or, respectively, ball-shaped or an ellipsoidal hollow body is formed. It is important in this context, as evident from the following, that by the round or curved shape of the loop 18a or the hollow body, respectively, the resistance during propulsion of the loop 18a or the hollow body with respect to the canal-shaped cavity to be examined is minimized. Furthermore, a cage provided at the end of the guiding wire 17a instead of the loop 18a or the hollow body is possible, as explained in the afore-described embodiment. However, as can be gathered from the functional description below, the loop 18a provided at the distal end of the guiding wire 17a does not necessarily have to be provided at the distal end of the guiding wire 17a. This loop 18a serves to assist during propulsion of the endoscope shaft 1.

The functioning or, rather, the drive mode of the continuous drive type endoscope in the canal-shaped cavity to be examined will be described hereinafter.

The endoscope is introduced into the canal-shaped cavity to be examined, preferably, by the guiding wire 17a projecting from the distal end portion of the endoscope shaft 1 or the loop 18a projecting from the distal end of the endoscope shaft 1. However, as long as the canal-shaped cavity comprises portions which are easy to pass, the guiding wire 17 or the loop 18a does not necessarily have to protrude beyond the distal end portion of the endoscope shaft 1. The endoscope is propelled by a drive means (not shown in FIG. 7) which may be a conventional drive means for continuous drive type endoscopes known from prior art. The drive means may either drive the catheter hose 16a, which is fixedly arranged on the endoscope shaft, or the endoscope shaft 1. Likewise a drive of both aforementioned elements is possible. That is, in more concrete terms, the endoscope shaft 1 can be driven by the drive means as long as the stiffness thereof is sufficient for moving the endoscope shaft 1 in the canal-shaped cavity. If the stiffness thereof is or becomes insufficient, the catheter hose 16a is controlled such that it acts as guiding means and as stiffness adjusting means increasing the stiffness by methods know by the prior art in order to reinforce the endoscope shaft in the axial direction thereof. Preferably, the stiffness of the catheter hose 16a is adjusted by introducing an elastic wire having optionally a loop 18a (but does not have to comprise a loop 18a) at its distal end portion in the catheter hose. Accordingly, the catheter hose 16a achieves the certain stiffness and elasticity of the elastic wire by glidingly accommodating the latter thereby guiding the endoscope shaft 1 and, at the same time, preventing the endoscope shaft from being bent excessively.

Another possibility of adjusting the stiffness of the catheter hose 16a is to introduce a fluid (a liquid or a gas) into the latter. According to the specific pressure applied to the fluid when introducing the fluid and maintaining the specific pressure in the catheter hose 16a, a certain stiffness of the catheter hose 16a corresponding to the certain pressure is obtained. In this case, when introducing a fluid into the catheter hose 16a, the distal end portion of the catheter hose 16a has to be closed (for example with a plug) so that the catheter hose is sealed fluid tightly. However, as mentioned above, any means for varying the stiffness of the catheter hose 16a known by the prior art may be used.

Referring again to the catheter hose 16a with the guiding wire 17a introduced therein shown in FIG. 7, corresponding to the power the endoscope shaft 1 is introduced into the canal-shaped cavity by the retained or fixed guiding wire 17a which does not slide in the catheter hose 16a at this time and which projects by the loop 18a thereof beyond the proximal end of the endoscope shaft by a predetermined distance, i.e. the guiding wire performs no relative movement with respect to the endoscope shaft 1 or the catheter hose 16a. However, as mentioned above, the loop 18a of the guiding wire 17a is not obligatory and merely serves to facilitate the propulsion of the endoscope shaft 1.

Upon reaching a curvature and/or bend of the canal-shaped cavity at which the protruding loop 18a of the guiding wire 17a arrives ahead of the endoscope shaft 1, the loop 18a contacts a curved outer wall of the canal-shaped cavity corresponding to the curvature. By virtue of the substantially circular or curved shape of the loop 18a, upon further propulsion it slides along the curved outer wall of the canal-shaped cavity. This ensures that the frictional resistance between the loop 18a of the guiding wire 17a and the curved outer wall is minimized during propulsion of the endoscope shaft 1. Due to the elasticity of the guiding wire 17a, it is bent at the curved outer wall of the canal-shaped cavity by the contact of the loop 18a. Accordingly, due to the elasticity of the guiding wire 17a which is bent in accordance with the curvature of canal-shaped cavity, also the endoscope shaft 1 is bent by the guiding wire 17a, thereby orientating the endoscope shaft 1 according to the curvature of the canal-shaped cavity. Furthermore, the endoscope shaft 1 is prevented from being bent excessively due to the accommodation of the elastic guiding wire 17a in the catheter hose 16a. Since the loop 18a of the guiding wire 17a leads the endoscope shaft 1 upon propulsion, the loop 18a already passes the bend and/or curvature before it is reached by the endoscope shaft and adapts or deforms the flexible endoscope shaft 1 in conformity with the shape of the curvature of the canal-shaped cavity. Thus the guiding wire including the loop 18a which is bent by the course of the curvature takes the lead of the endoscope shaft 1 as well as the orientation thereof which follows the loop 18a.

As mentioned already in the foregoing, during propulsion the endoscope shaft 1 takes up forces in the radial direction as well as in the axial direction thereof which act from the catheter hose 16*a* via the supports 16*b* on the endoscope shaft 1 and from the drive means during propulsion. Further the endoscope shaft 1 is bent by virtue of passing the bend or curvature. In order to prevent the highly flexible endoscope shaft 1 from excessively curving, the catheter hose 16*a* acting as guiding means and as stiffness adjusting means is capable of varying the flexural strength thereof. In this way a sufficient flexibility of the endoscope shaft can be brought about and at the same time buckling of the endoscope shaft can be prevented. For example, when using the guiding wire 17*a*, also the stiffness of the catheter hose 16*a* accommodating the guiding wire 17*a* is changed and therefore acts as guiding and stiffness adjusting means. Also it is possible during propulsion of the endoscope shaft 1, to use guiding wires 17*a* having a different stiffness and elasticity, respectively, dependent on the degree of the curvature the endoscope shaft 1 has to pass. Accordingly, an accurate stiffness of the endoscope shaft 1 is provided.

Thus, when using the guiding wire 17*a* with the loop 18*a*, even portions which are difficult to pass in the canal-shaped cavity, such as e.g. bends and/or curvatures, can easily be passed by means of the guide wire 17*a* including the loop 18*a* formed at the leading end thereof.

As one can take from the afore-described drive mode of the continuous drive type endoscope, the loop 18*a* acts as a kind of leading guide element of the guiding wire 17*a* with respect to the endoscope shaft 1 which facilitates the movement of the endoscope shaft 1. The design of the loop 18*a* enables the same to follow the curvatures and/or bends of the canal-shaped cavity.

Upon reaching the location to be examined in the canal-shaped cavity, the guiding wire 17*a* including the loop 18*a* can be withdrawn so as to avoid hindering of an appropriate medical treatment/examination carried out by the various means 3 of the endoscope head 2 of the endoscope shaft 1. Accordingly, the respective medical treatment/examination can be carried out without any difficulties.

(Further Possible Variations)

Finally it is pointed out that the present description and the enclosed figures only have an exemplary character and by no means are intended to restrict the invention to the submission made here. The invention permits a plurality of applications and modifications without leaving the core of the invention.

Hereinafter some modifications are mentioned:

Basically, the afore-described principle of the alternating propulsion of the endoscope can be started and stopped again in any state of the forward movement of the endoscope. That is to say, the endoscope shaft and the auxiliary means first can be moved into the canal-shaped cavity and the alternating propulsion is only started at a particular position of the cavity which is difficult to pass. After passing this position (e.g. strong bends of the cavity) it is also possible to deactivate and again activate the alternating propulsion during further forward movement.

In the first embodiment the shape of the fluid pads has been specified. Any other shape of the fluid pads is possible, however. For instance, the fluid pads could be in the form of a ring surrounding the hose 5 in a plane normal to the longitudinal axis of the hose. The ring should be hollow inside and should be divided into several chambers. Each of the individual chambers formed in this way would then correspond to the function of a fluid pad 6 and, similarly to the fluid pads, pressure would have to be supplied and relieved through feed lines.

Moreover fluid pads 6 can also be completely dispensed with and the flexibility is varied via canal-shaped cavities extending in the longitudinal direction at the outer circumference, at the inner circumference or in the wall of the hose and/or the auxiliary means. Furthermore these canal-shaped cavities could be helically formed at the outer circumference, at the inner circumference or in the wall of the hose and/or the auxiliary means. Likewise variation of the flexibility of the endoscope shaft 1 can preferably be realized by means of these canal-shaped cavities extending in the longitudinal direction or helically along the endoscope shaft 1 by arranging the canal-shaped cavities at the outer circumference, in the radically outer area or in a working conduit. For varying the flexibility of the auxiliary means and/or the endoscope shaft, pressure is applied to or relieved from the fluid or medium provided in the cavities or the physical state of the medium is changed, as will be described later.

The length of the leading end portion of the hose 5 along which the fluid pads 6 are arranged is approximately 50 cm in the first embodiment. However, it is obvious that the length of this leading end portion can be appropriately varied.

Moreover, in the first embodiment the fluid pads 6 are arranged at the outer circumference of the hose 5. But it is likewise possible to embed the fluid pads in the hose wall.

Alternatively to the hose 5, a spiral spring could be used in the first embodiment. This spiral spring could be used as an auxiliary means with or without fluid pads arranged at the outer circumference.

In the first embodiment, the fluid pads have been arranged in groups of three fluid pads. The number of fluid pads for each group can also be increased, however.

As another modification of the first embodiment the fluid pads 6 could vary the flexibility of the hose 5 by the fact that thermal elements are arranged in the respective fluid pads and the fluid pads 6 are filled with a medium which varies its physical state of matter from solid to liquid by heating by means of the thermal elements. In this way, by heating the respective thermal elements, whereby the medium is in a liquid state, the hose 5 could be equipped with a lower flexibility than the endoscope shaft 1. By deactivating the thermal elements the medium in the fluid pads could be solidified, thereby the hose 5 having a lower flexibility than the endoscope shaft 1. The same principle is valid if a medium is used which changes its state from liquid to gaseous when heated by means of the thermal elements.

The variation of flexibility of the hose 5 by means of pressure application or relief of the fluid pads 6 described in the first embodiment can also be performed in several steps or even continuously. That means the application of pressure to the fluid pads 6 could be controlled such that the higher the pressure applied, the farther the endoscope head 2 is moved forward in a cavity bend while the hose 5 is resting, i.e. the more the deflecting 4 is curved during the forward movement.

In the first embodiment, in the retracted state of the endoscope shaft 1 (state of FIG. 3*a*) the leading end (distal end) of the hose 5 ends with the trailing end of the deflecting 4. However, the present invention is not restricted thereto and the leading end of the hose 5 can also end further behind the deflecting 4 in the retracted state of the endoscope shaft 1.

Since the hose 5 is preferably manufactured of a highly flexible EPTFE material, the hose can be strongly expanded without varying its diameter and/or its wall thickness. Therefore, for instance the hose 5 in the first embodiment can reach up to the endoscope head 2 and can there be fastened to the same in a fluid-tight manner (e.g. by gluing). This state is shown in FIG. 5*a*, wherein it has to be noted that the endoscope is represented in the longitudinal section in the FIGS.

5a to 5c right from the line I-I. In the retracted state of the endoscope shaft 5 (state of FIG. 5a), the fluid pads 6 are arranged behind the deflecting 4.

Figure 5:
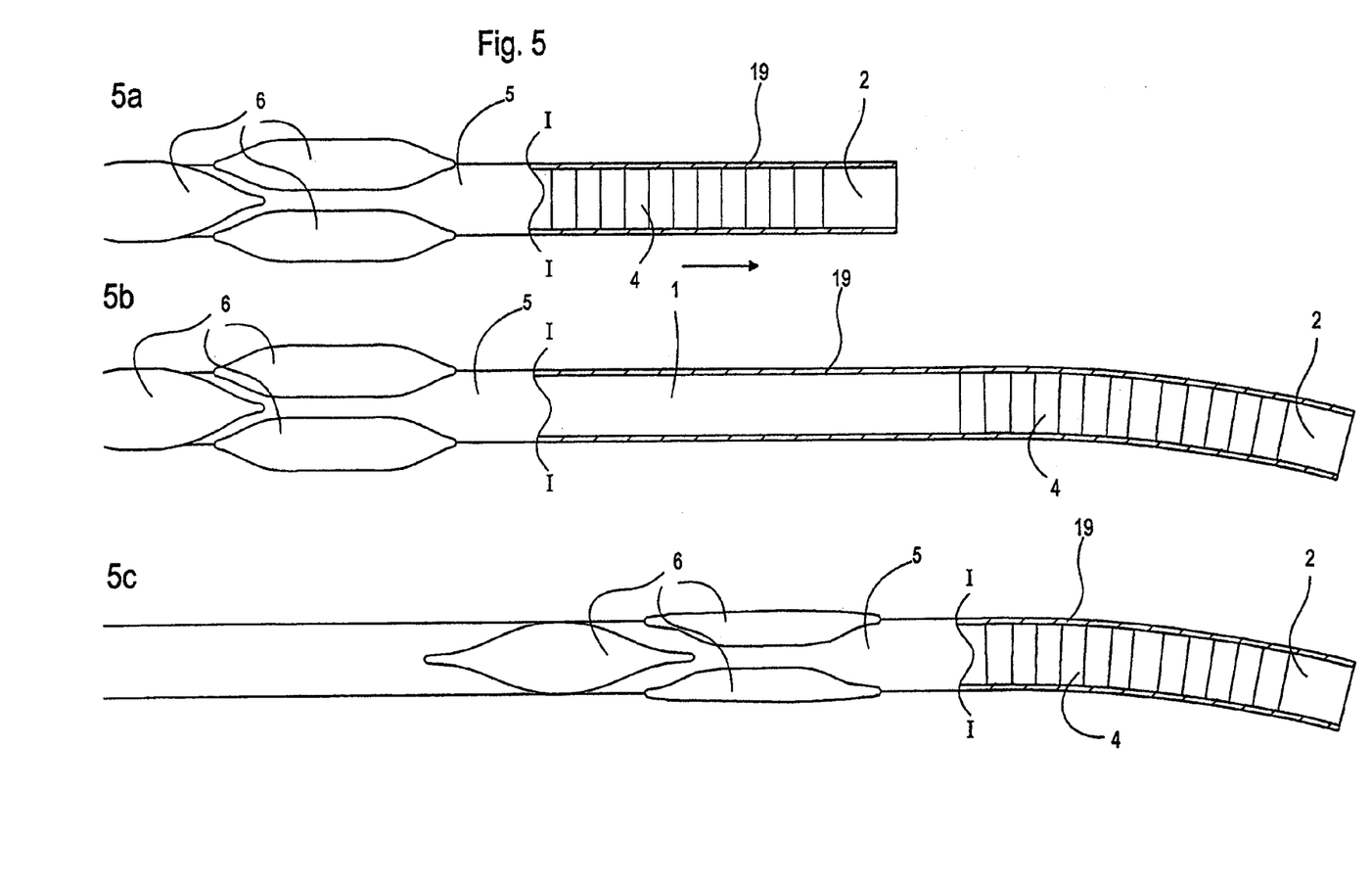
FIGS. 5a to 5c are front views of the endoscope illustrating the progressive movement of the endoscope according to a modification of the first embodiment.

If only the endoscope shaft 1 is moved forward, as shown in FIG. 5b, while pressure has been applied to the fluid pads and thus they are resting with respect to the cavity wall, an expansion portion 19 of the hose 5 at which no fluid pads 6 are arranged is expanded relative to the hose 5 by the forward movement of the endoscope shaft 1. During this expansion the leading end of the expansion portion 19 is fixed at the endoscope head 2 moving forward and the trailing end of the expansion portion 19 is fixed vis-à-vis the cavity wall by the fluid pads 6 pressing against the cavity wall.

If the hose 5 is moved forward with relieved fluid pads 6, as shown in FIG. 5c, the expansion portion 19 of the hose 5 contracts again.

This modification has to be understood as an addition to the first embodiment and has the advantage that the clearance between the endoscope shaft 1 and the hose 5 is closed so that neither lubricating material can escape from the clearance nor can impurities penetrate the clearance.

In the first embodiment the endoscope shaft 1 has been driven, during the propulsion of the hose 5 by the first drive unit 10, at the same speed in the opposite direction by the second drive unit 14.

Alternatively to the opposite drive of the endoscope shaft 1 by the first drive unit 14, the endoscope shaft 1 could also be fastened with respect to the cavity wall to the leading end thereof by means of the deflecting 4 and the first drive unit 14 could be switched to idling so that the drive wheels 13 can rotate freely. Thus the endoscope shaft 1 would likewise be resting vis-à-vis the cavity wall, while the hose 5 is moved forward.

It would be another alternative not to connect the hose 5 to the plate 12. In that case the trailing end of the hose 5 has to be spaced apart from the plate 12 in the state in which the hose 5 is in its leading position with respect to the endoscope head 2 by a distance by which the endoscope shaft 1 moves forward during the movement cycle. With the propulsion of the endoscope shaft 1 in this alternative, the trailing end of the hose 5 would be arranged close to the plate 12 and the drive wheels 11 of the first drive unit 10 would be at rest so that the hose 5 rests with respect to the cavity wall. During propulsion of the hose 5, however, the second drive unit 14 would be at rest so that the drive wheels 13 do not rotate. The bulged shape 15 would not be varied in size during this forward movement of the hose 5 and the trailing end of the hose 5 would move simultaneously with the propulsion into the cavity also away from the plate 12.

In the first embodiment the variation of flexibility of the hose 5 by means of the fluid pads 6 has been described. In addition or as an alternative to that, also the flexibility of the endoscope shaft can be varied by fluid pads arranged at the outer circumference of the endoscope shaft or integrated in the outer circumference. The supply lines for these fluid pads of the endoscope shaft would have to extend backwards inside the endoscope shaft to the operating end. The alternating propulsion according to this modification is performed in accordance with the same functioning as the first embodiment, wherein the temporarily stiffer element of endoscope shaft and hose supports the simultaneously more flexible element during the forward movement.

Although the second embodiment dispenses, as described above, with the use of a hose 5 including fluid pads 6, also a combination of the first and second embodiments is possible.

An embodiment not described in more detail works advantageously by advancing the described endoscope shaft, the described hose and the described guiding wire in an alternating manner. In this embodiment the endoscope basically has the afore-described design, wherein, apart from the endoscope shaft, the hose and the guiding wire including pertinent drive units for advancing are provided.

In this embodiment first of all the endoscope shaft is advanced and subsequently the hose is pulled along for supporting the shaft, i.e. it is likewise advanced by the drive unit in a comparable manner. In this way, the endoscope can be brought into the desired position. However, in the case of narrow curves problems of maneuvering the endoscope shaft around the movement of such a narrow curve may arise. In this case, initially the guiding wire possibly including a cage which is easier to maneuver around narrow bends can be advanced. After that the endoscope shaft is guided around the curve by tracking. Consequently, in this case first the guiding wire, possibly including a cage, is advanced and then the endoscope shaft is tracked, i.e. likewise advanced by the drive unit. In a next step the hose can be pushed to stabilize the endoscope shaft. By this alternating movement of the three elements the endoscope can be safely maneuvered even around narrow curves and bends.

Figure 6:
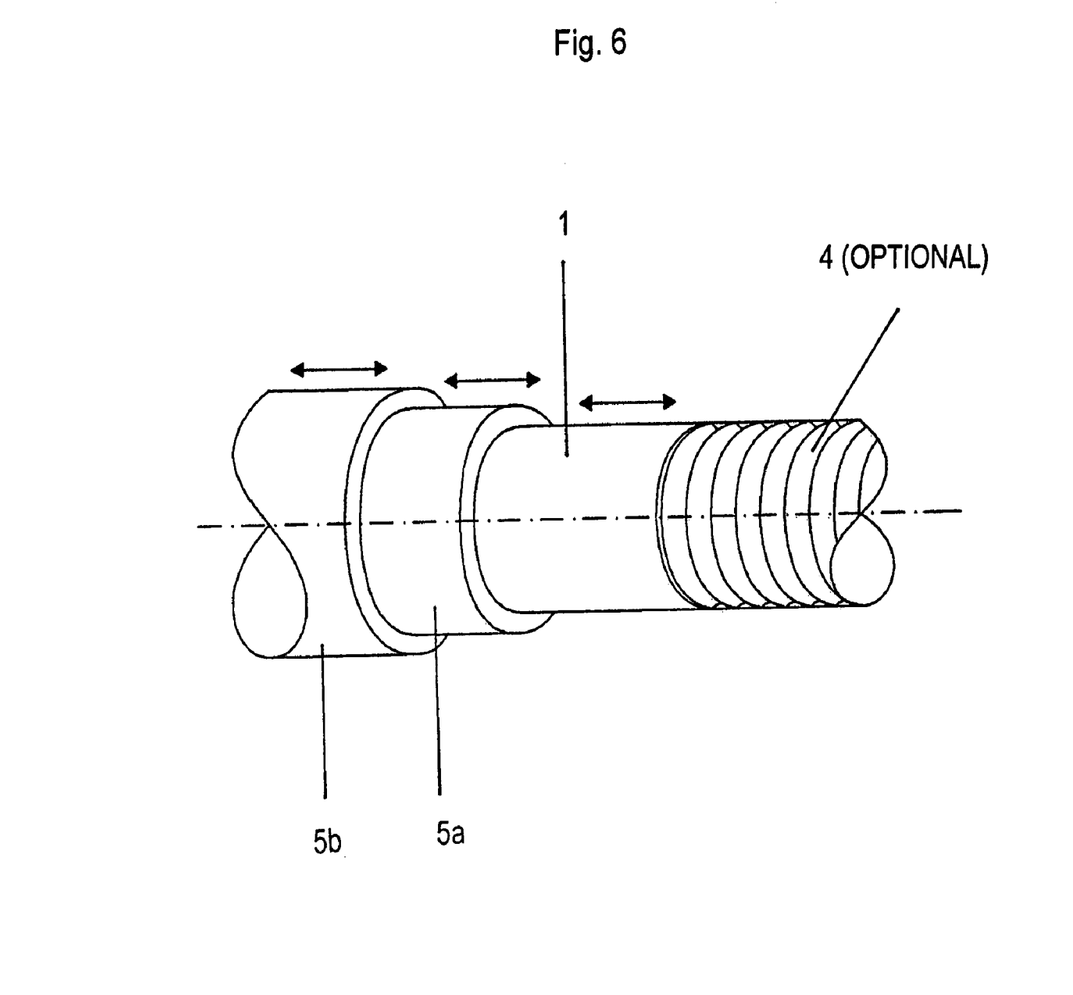
FIG. 6 shows a third preferred embodiment of the invention.

Hereinafter a third preferred embodiment of the invention is described by way of FIG. 6.

In this embodiment the auxiliary means consists of a plurality of (preferably two) hoses which, being movable relative to each other and positioned one inside the other, surround the endoscope shaft at least in portions. The total stiffness of the plurality of hoses is higher than that of the endoscope shaft, wherein the stiffness of preferably each individual hose is lower than that of the endoscope shaft.

If the endoscope shaft is to be driven into a cavity, the plurality of hoses has to be retained in a first step, while the endoscope shaft is moved forward over a certain distance relative to the hoses. The hoses in their entirety serve as a guide for the shaft. After that the shaft is retained, while the hoses are successively pushed forward, i.e. each per se, the shaft having a higher basic stiffness than the individual hoses serving as a guide and accordingly taking up guiding forces.

Finally it is pointed out that the foregoing embodiments are mentioned in connection with two drive units 10 and 14. These are not absolutely necessary. It is completely sufficient, for instance, to drive only the shaft by a motor and to retain the auxiliary means temporarily by a clamping means or a brake, for instance. The tracking of the auxiliary means is then carried out manually while the shaft is retained. It is also possible to perform both movements only manually.

An endoscope preferably comprising an alternating propulsion system in which an endoscope shaft is advanced by means of an auxiliary means (e.g. a hose preferably including fluid pads or a guiding wire/net) in a canal-shaped cavity by the fact that the endoscope shaft and the auxiliary means are alternately resting with respect to a cavity to be inspected and, at the same time, the element not at rest can be advanced while being guided along the resting element into the cavity, or are simultaneously moved forward, wherein in the latter case the basic stiffness of the auxiliary means is higher than that of the shaft.

The invention claimed is:

1. An alternating propulsion type endoscope, comprising:
   an endoscope shaft having a base flexibility; and
   a hose surrounding at least a portion of the endoscope shaft and having a variable flexibility, wherein the hose comprises a wall having an inner surface, an outer surface and a plurality of hose cavities at least one of the inner surface, the outer surface or within the wall, wherein each of the hose cavities is at least one of a canal or a fluid pad that can be variably filled with a medium having a pressure, wherein the pressure is variable to change the variable flexibility from a first temporary flexibility to a second temporary flexibility, wherein the hose cavities are radially extendable to contact a canal-shaped body cavity, wherein the first temporary flexibility is greater than the base flexibility and the second temporary flexibility is less than the base flexibility, wherein the endoscope is adapted to be propelled into the body cavity, to be inspected by alternately retaining one of the endoscope shaft or the hose with respect to the body cavity and simultaneously propelling the other one of the endoscope shaft or the hose, and wherein the endoscope shaft is guided along the hose when the endoscope shaft is not retained, and the hose is guided along the endoscope shaft when the hose is not retained, wherein flexibility of the endoscope shaft is variable by varying the pressure of the medium provided in the hose cavities, wherein the hose cavities are arranged such that at least one of the hose cavities is circumferentially offset and longitudinally displaced from a second of the hose cavities, wherein one or more of the hose cavities includes a tongue, wherein a first tongue of a first one of the hose cavities and a second tongue of a second one of the hose cavities are aligned parallel to each other about an outer circumference of the shaft at a same longitudinal position of the shaft.

2. An endoscope according to claim 1, wherein the hose auxiliary means forms a guide extending along the endoscope shaft at least in portions.

3. An endoscope according to claim 1, wherein the flexibility of the endoscope shaft is variable at least temporarily.

4. An endoscope according to claim 1, wherein the endoscope shaft has a curvature that is adjustable at least at a leading end portion of the endoscope shaft.

5. An endoscope according to claim 1, wherein the hose can be brought into an idle position with respect to a wall of the body cavity by pressing against the wall of the body cavity.

6. An endoscope according to claim 1, wherein the plurality of hose cavities overlap at least partly in a longitudinal direction of the hose.

7. An endoscope according to claim 1, wherein the plurality of hose cavities are arranged at least at a leading end portion of the hose.

8. An endoscope according to claim 1, wherein the endoscope shaft is provided with hollow spaces in a form of duct or fluid pads which are adapted to be filled or are filled with a medium for a temporary stiffening of the endoscope shaft.

9. An endoscope according to claim 1, wherein the flexibility of the hose changes between the first variable flexibility and the second variable flexibility by changing the physical state of the medium provided in the hose cavities.

10. An endoscope according to claim 7, wherein a distal end of the hose is fastened to an endoscope head provided at a distal end of the endoscope in a fluid-tight manner.

11. An endoscope according to claim 1, wherein the relative flexibility between the base flexibility and the variable flexibility is variable by changing the physical state of the medium provided in the hose cavities.

12. An endoscope according to claim 1, wherein the first one of the hose cavities and the second one of the hose cavities are longitudinally displaced.

13. An endoscope according to claim 1, wherein a greater number of the hose cavities are aligned parallel to each other about an outer circumference of the shaft at the tongues than at a central portion of the hose cavities.

14. An endoscope according to claim 1, wherein the tongue of at least one of the hose cavities is irremovably coupled to the shaft at a first location and a central portion of the hose cavity is coupled to the shaft at a second location, wherein the first location and the second location are different.

15. An endoscope according to claim 1, wherein an increase in pressure changes the first temporary flexibility to the second temporary flexibility and a decrease in pressure changes the second temporary flexibility to the first temporary flexibility.

16. A continuous drive type endoscope, comprising:
an endoscope shaft having an outer circumference and a first stiffness;
a guiding means having a second stiffness; and
a stiffness adjusting means,
wherein upon propulsion of the endoscope shaft into a canal-shaped cavity to be examined, the guiding means guides the endoscope shaft,
wherein the stiffness adjusting means is to vary the stiffness of the guiding means depending on the cavity to be examined, and
wherein at least one of the guiding means or the stiffness adjustment means is arranged at the outer circumference of the endoscope shaft, wherein the stiffness adjustment means includes a plurality of fluid pads or canals that are filled with a variable amount of a medium to vary a pressure within the plurality of fluid pads or canals to directly vary the second stiffness between a first state where the second stiffness is less than the first stiffness to a second state where the second stiffness is greater than the first stiffness,
wherein the first stiffness is variable by varying the pressure of the medium provided in the plurality of fluid pads or canals of the stiffness adjusting means varying the stiffness of the guiding means,
wherein the plurality of fluid pads or canals are arranged such that at least one of the plurality of fluid pads or canals is circumferentially offset and longitudinally displaced from a second of the plurality of fluid pads or canals, and wherein one or more of the fluid pads or canals includes a tongue-shaped end portion,
wherein a first tongue portion of a first one of the plurality of fluid pads or canals and a second tongue portion of a second one of the fluid pads or canals are aligned parallel to each other about an outer circumference of the endoscope shaft at a same longitudinal position of the endoscope shaft.

17. An endoscope according to claim 16, wherein the guiding means is a guiding wire including a foldable cage arranged at the leading end of the guiding wire.

18. An endoscope according to claim 17, wherein the cage is tapered toward a front end.

19. An endoscope according to claim 16, wherein a flexural strength of at least one the guiding means or the stiffness adjusting means is variable.

20. An endoscope according to claim 19, wherein at least one the guiding means or the stiffness adjusting means is a hose in which a guiding element is glidingly supported.

21. An endoscope according to claim 19, wherein at least one the guiding means or the stiffness adjusting means is disposed at the endoscope shaft.

22. An endoscope according to claim 21, wherein at least one the guiding means or the stiffness adjusting means is arranged at a circumference or in an interior of the endoscope shaft and extends in a longitudinal direction of the endoscope shaft.

23. An endoscope according to claim 16, wherein at least one the guiding means or the stiffness adjusting means comprises a guiding wire, the guiding wire further comprising a loop which is provided at one end of the guiding wire and projects from a distal end portion of the endoscope shaft.

24. An alternating propulsion type endoscope, comprising:
an endoscope shaft;
a hose;
a first fluid pad;
a second fluid pad; and
a third fluid pad,
wherein the endoscope is adapted to be propelled into a canal-shaped body cavity to be inspected by alternately retaining one of the endoscope shaft or one or more of the first fluid pad, the second fluid pad or the third fluid pad with respect to the body cavity and simultaneously propelling the other one of the endoscope shaft or one or more of the first fluid pad, the second fluid pad or the third fluid pad, and
wherein each of the fluid pads has a variable pressure which, when varied, inversely varies the flexibility of the hose between a first state where the hose is more flexible than the shaft and a second second state where the hose is less flexible than the shaft.

25. An endoscope as defined in claim 24, wherein the second fluid pad and the third fluid pad are circumferentially displaced and longitudinally aligned with respect to each other, and
wherein the first fluid pad is circumferentially displaced and longitudinally displaced from the second fluid pad and the third fluid pad so that a first portion of the first fluid pad longitudinally aligns with a portion of the second fluid pad and a portion of the third fluid pad and a second portion of the first fluid pad does not longitudinally align with the second fluid pad or the third fluid pad.

* * * * *